United States Patent [19]

Manogue

[11] Patent Number: 4,973,713
[45] Date of Patent: Nov. 27, 1990

[54] CATALYTIC HYDROGENATION OF CARBOXYLIC ANHYDRIDES TO ESTERS OR LACTONES

[75] Inventor: William H. Manogue, Newark, Del.

[73] Assignee: E. I. du Pont de Nemours and Company, Wilmington, Del.

[21] Appl. No.: 442,097

[22] Filed: Nov. 28, 1989

[51] Int. Cl.[5] .................. C07D 307/32; C07D 239/02
[52] U.S. Cl. .................................. 549/307; 549/302; 549/311; 549/325; 549/326; 560/1; 560/106; 560/122; 560/265; 544/321
[58] Field of Search .............. 549/302, 307, 311, 325; 560/1, 106, 122, 265; 544/321

[56] References Cited

U.S. PATENT DOCUMENTS

| | | | |
|---|---|---|---|
| 3,957,827 | 5/1976 | Lyons | 260/343.3 R |
| 4,048,196 | 9/1977 | Broecker et al. | 549/325 |
| 4,096,156 | 6/1978 | Freudenberger et al. | 549/325 |
| 4,155,919 | 5/1979 | Ramioulle et al. | 549/325 |
| 4,192,807 | 3/1980 | Broecker et al. | 549/325 |
| 4,211,711 | 7/1980 | Fuenten et al. | 260/343.3 R |
| 4,356,337 | 10/1982 | Pez et al. | 585/267 |
| 4,420,325 | 12/1983 | Sauers | 544/321 |
| 4,485,245 | 11/1984 | Hsu et al. | 549/302 |
| 4,485,246 | 11/1984 | Lyons | 549/302 |
| 4,528,385 | 7/1985 | Fuenten et al. | 549/307 |
| 4,609,636 | 9/1986 | Mabry et al. | 502/185 |
| 4,678,500 | 7/1987 | Hay et al. | 544/321 |
| 4,772,729 | 9/1988 | Rao | 549/326 |
| 4,782,167 | 11/1988 | Rao | 549/326 |

FOREIGN PATENT DOCUMENTS 467656 9/1935 United Kingdom .
2194232 3/1988 United Kingdom ............... 549/325

OTHER PUBLICATIONS

Kirk–Othmer, Encyclopedia of Chemical Technology (3rd Ed.), vol. 9, p. 321.
Encyclopedia of Polymer Science & Engineering (2nd Ed.), vol. 12, pp. 36–40.
Supplement B, The Chemistry of Acid Derivatives—Part 1, J. Wiley & Sons, New York, Chapter 7.
Supplement B, The Chemistry of Acid Derivatives—Part 2, J. Wiley & Sons, New York, pp.. 1138–1145.
P. R. Austin et al., J. Am. Chem. Soc., 1937, 59; 864.
Hanagan et al., CA 103-178272y (1985).
Sauers, CA 98-16731y (1983).
Hay et al., CA 109-124410x (1988).
Kato et al., CA 106-115250f (1987).
Raslervis et al., CA 104-83798f (1986).

Primary Examiner—Cecilia Shen

[57] ABSTRACT

A process for the production of esters or lactones, comprising reacting in the presence of a catalyst and under hydrogenation conditions hydrogen and an acyclic or cyclic carboxylic anhydride to produce the corresponding ester or lactone, wherein the catalyst is a supported catalyst comprising:

(a) a group VIII metal, Re and Fe;
(b) a group VIII metal on $TiO_2$;
(c) Ru and at least one of Re, Ag or Cu; or
(d) Pd and Fe.

Preferably, the anhydride has the formula

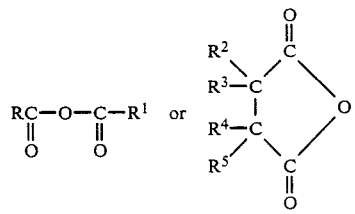

and is reacted to form an ester of the formula

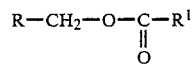

or a lactone of the formula

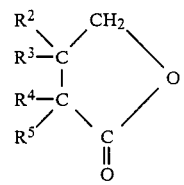

wherein R and $R^1$ independently are lower alkyl or cycloalkyl; $R^2$, $R^3$, $R^4$, $R^5$ independently are hydrogen, lower alkyl, cycloalkyl or aryl; and wherein $R^3$ and $R^4$ taken together may form a saturated or unsaturated ring, or an aromatic ring. The more preferred starting material is phthalic anhydride.

18 Claims, No Drawings

CATALYTIC HYDROGENATION OF CARBOXYLIC ANHYDRIDES TO ESTERS OR LACTONES

BACKGROUND OF THE INVENTION

Esters and lactones, produced from acyclic and cyclic carboxylic anhydrides, have utility as intermediates in various dye, pharmaceutical and agricultural chemical syntheses, as well as in the production of lacquers, paints, varnishes and plasticizers, see, e.g., Kirk-Othmer, Encyclopedia of Chemical Technology (3rd Ed.), vol. 9, page 321. Lactones, in particular, are useful in polymerization processes, i.e., ring-opening polymerization, Encyclopedia of Polymer Science & Engineering, Vol. 12, pages 36–40 (2nd Ed.).

Currently, however, known processes for the production of esters or lactones from acyclic and cyclic carboxylic anhydrides require expensive catalysts, solvents that are expensive and/or difficult to handle, or both. Supplement B, The Chemistry of Acid Derivatives—Part 1, J. Wiley & Sons, New York, Chapter 7, reviews the synthesis of esters; ibid., Part 2, pages 1138–1145, reviews the reduction of anhydrides.

P. R. Austin et al., J. Am. Chem. Soc., 1937, 59; 864, disclose a method for the preparation of phthalide from phthalic anhydride by hydrogenation over a copper chromite catalyst at 270° C. and 20.7–24.1 MPa of hydrogen, in the absence of a solvent, obtaining phthalide in 15 to 56% yield.

U.S. Pat. No. 4,485,245 and U.S. Pat. No. 4,485,246 to Lyons disclose a process for the homogeneous hydrogenation of phthalic anhydride to phthalide in unspecified yield.

U.S. Pat. No. 4,211,711, to Fuenten et al., discloses a method for the preparation of phthalide by the catalytic hydrogenation of a phthalide substituted in the 3-position by a hydroxy, methoxy or acetoxy group. The patent employs a group VIII metal catalyst in an inert organic solvent, preferably an alcohol, and obtains a product in up to 99% yield.

U.S. Pat. No. 4,528,385, also to Fuenten et al., discloses a method for the preparation of phthalide in 85% yield from phthalic anhydride using a nickel catalyst and a benzoic acid ester as the solvent. The reaction takes place at 150° C. and 3.0 MPa of hydrogen.

British Patent No. 467,656 discloses catalytic hydrogenation of a phthalic anhydride to phthalide using a hydrogenating metal associated with an acidic oxide of (for example) titanium, preferably in a lower state of valency. They also disclose the presence of a solvent to be essential to high conversions.

U.S. Pat. No. 4,772,729 discloses preparation of 3-substituted tetrahydrofuran and 3- and 4-substituted butyrolactones by hydrogenating appropriate precursor materials in the presence of a catalyst containing palladium, rhenium and at least one support which is titanium dioxide, zirconium oxide or carbon.

U.S. Pat. No. 4,782,167 discloses preparation of butyrolactones and butane diols by hydrogenating the appropriate precursor in the presence of a catalyst containing palladium or palladium/rhenium on a titanium, zirconium or hafnium oxide support.

SUMMARY OF THE INVENTION

This invention provides a process for the production of esters or lactones from acyclic or cyclic carboxylic anhydrides, using a relatively low-cost catalyst and requiring no solvent or only inexpensive solvents for the reaction to proceed.

Thus, in one aspect, this invention provides a process for the production of esters or lactones from acyclic or cyclic carboxylic anhydrides, comprising under hydrogenation conditions reacting hydrogen and an acyclic or cyclic carboxylic anhydride in the presence of a catalyst:

(a) a group VIII metal, rhenium and iron;
(b) a group VIII metal on a $TiO_2$ support;
(c) ruthenium and at least one of rhenium, silver or copper; or
(d) palladium and iron on carbon.

DETAILED DESCRIPTION OF THE INVENTION

Preferably, the carboxylic anhydride has the formula:

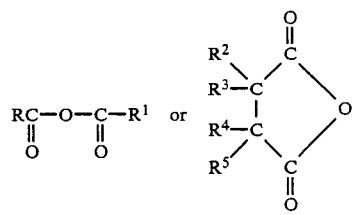

and accordingly is reacted to form an ester of the formula

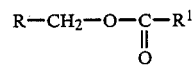

or a lactone of the formula

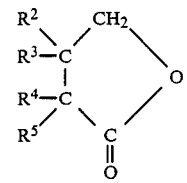

wherein R and $R^1$ independently are $C_1$–$C_8$-alkyl or $C_5$–$C_{15}$-cycloalkyl; $R^2$, $R^3$, $R^4$, $R^5$ independently are hydrogen, $C_1$–$C_8$-alkyl, $C_5$–$C_{15}$-cycloalkyl or $C_6$–$C_{18}$-aryl; and wherein $R^3$ and $R^4$ taken together may form a $C_5$–$C_{15}$-saturated or unsaturated ring, or an aromatic ring.

While support is not required for the process to function with catalysts (a) and (c), it is preferred to allow the active phase to be dispensed in the form of small crystallites whose surfaces provide a sufficient number of active sites. Preferred supports include carbon, $Al_2O_3$, $SiO_2$, $TiO_2$ and $La_2O_3$, as well as zinc oxide, lanthanum oxide or a mixture thereof. Where the catalyst is a group VIII metal, rhenium and iron, a carbon support is especially preferred.

Group VIII metals in (a) are the "noble" metals, specifically ruthenium, rhodium, palladium, osmium, iridium and platinum. Palladium is especially preferred. Preferred catalysts include Pt/Re/Fe, preferably on a carbon support, Pd on $TiO_2$, Pd/Re on $TiO_2$, Ru on TiO$_2$ and Ru/Ag on SiO$_2$. Mixtures of group VIII metals may be used.

Group IA or Group IIA metals may also be included in (a). In this embodiment, preparation of the catalyst is carried out in the presence of IA or IIA metals, such as potassium, sodium, lithium, calcium or magnesium. The latter may be present in the support as obtained or may be added, if absent, by impregnating the support with a solution of a Group IA or IIA metal compound, e.g., LiCl, NaCl, KCl, KOH, NaOH, CaCl$_2$, or MgCl$_2$·6H$_2$O. It is believed that the Group IA or IIA metal has a beneficial effect on the catalyst microstructure.

Preferably, the noble metals in (a) are present in an amount of about 0.1 to 10% by weight of the total catalyst, rhenium is present in an amount of about 0.2 to 10% by weight of the total catalyst, and iron is present in an amount of 0.001 to 1% by weight, based on total catalyst and calculated as FeCl$_3$. The amount of iron is preferably that which gives optimum selectivity to the desired product, e.g., by blocking more active catalyst sites, which sites promote more extensive hydrogenation. Optimization of the amount of hydrogen can be performed by one of ordinary skill in the art, in view of applicants, disclosure, using thereafter standard testing protocol. Preferably, the group VIII metal in (b) is present in an amount of about 0.1–20% by weight, more preferably 0.1–10% by weight. Preferably, the amount of ruthenium in (c) is 0.5–5% by weight where rhenium is present, and 0.1–20% by weight where copper and/or silver are present. Preferably, rhenium where present in (c) is present in an amount of 1–9% by weight and copper or silver, where present, are present in an amount of 0.01–50% by weight, more preferably 0.1–5% by weight. Preferably, palladium is present in (d) in an amount of 0.02–10% by weight, more preferably 0.5–3% by weight. Iron in (d) is preferably present in an amount of 0.001 to 1% by weight, based on total catalyst and calculated as FeCl$_3$.

Preferred starting materials include cyclic carboxylic anhydrides, most preferably phthalic anhydride.

Preferred reaction solvents include polar solvents such as C$_{1-4}$-alcohols and water. The reaction may further be run neat, e.g., in molten phthalic anhydride. Preferably, the hydrogenation is conducted for 0.25–48 hours and at about 100°–300° C., more preferably 150°–250° C. Preferably, the hydrogen pressure is about 0.45 to 17.3 MPa, and preferably 3.4–5.3 MPa.

The catalysts of (a) may be prepared as described in U.S. Pat. No. 4,609,636, substituting other group VIII metals for Pd as desired. Any metal salt which can be brought into solution may be used to make the catalyst The metal in the active catalyst is formed by reduction with hydrogen either prior to or during the reduction of the organic feed.

The hydrogenation process may be conducted in batch or continuous mode, and may be conducted in liquid or vapor phase, or with reduction of a solid species by first dissolving in a suitable solvent. Flexibility in operation with the catalysts of the invention allows operation without the addition of solvent or with the use of only water as a solvent. The catalyst may be employed in either fixed bed reactors or slurry reactors using particle sizes well known to those skilled in the art. Slurry type reactors are preferred when the catalyst particle size has to be kept small and when temperature control is critical (see, Bisio and Kabel "Scale Up of Chemical Processes", Wiley-Interscience (1985)).

In particular, therefore, the process of the invention is useful for producing phthalide from phthalic anhydride. Phthalide may be used to produce, e.g., 2-[[[[[(4,6-dimethoxy-2-pyrimidinyl)amino]carbonyl]amino]sulfonyl]-methyl]-benzoic acid, methyl ester (Londax®), a rice herbicide, according to the following synthesis:

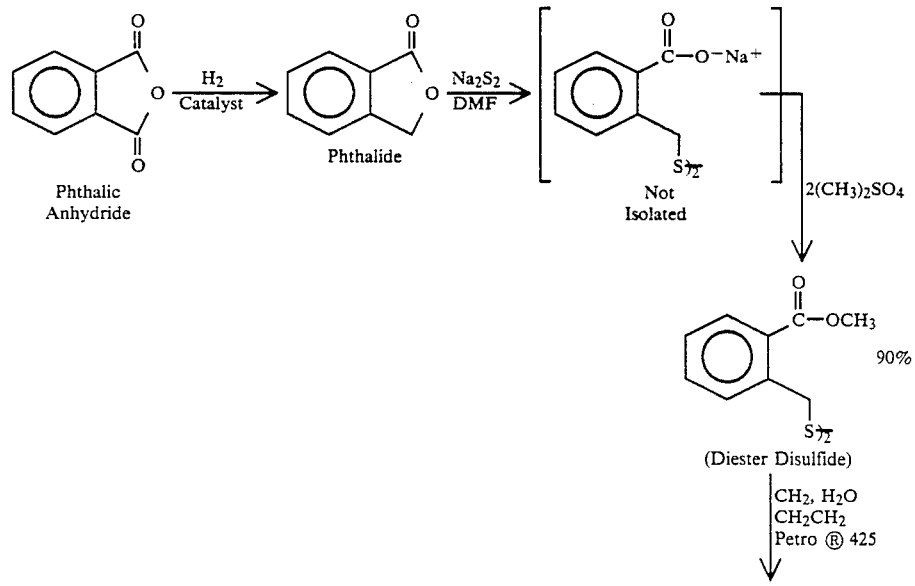

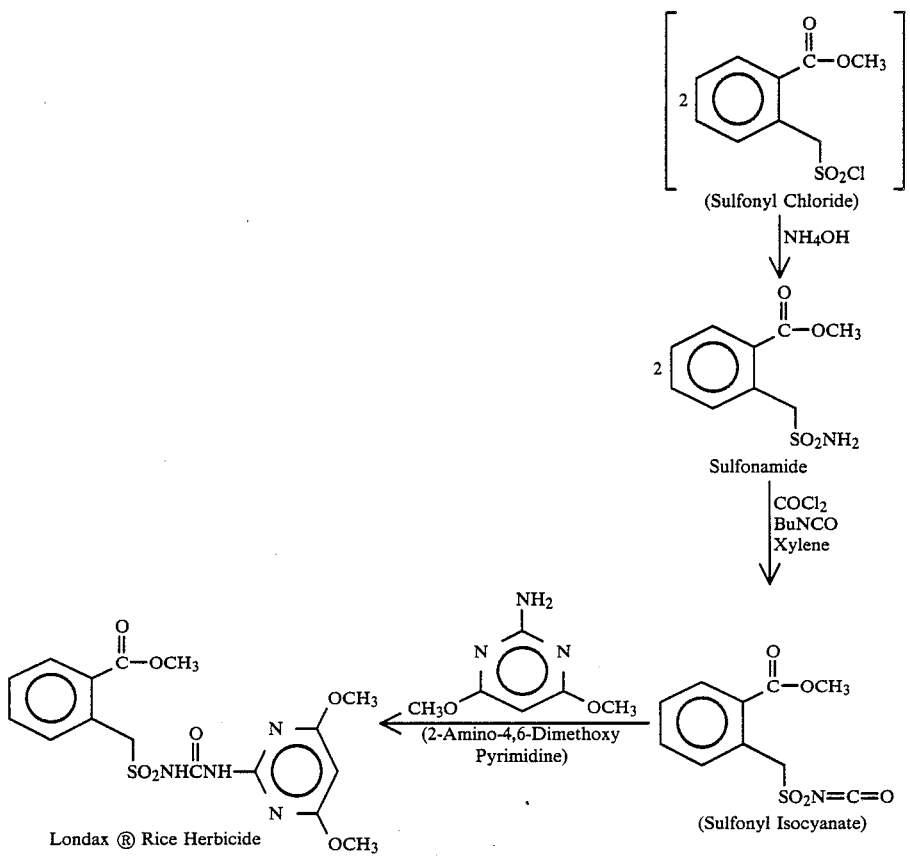

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications cited above and below are hereby incorporated by reference.

EXAMPLES

In the following examples, product compositions are listed in percent by weight, the iron salt added is $FeCl_3$, and the reaction time is 16 hrs., unless otherwise noted.

General Procedure for Hydrogenation

The reactor, a 400 mL glass-lined shaker tube was charged with phthalic anhydride (20 g), catalyst (1 g), and $FeCl_3$. The reactor was flushed twice with 0.69 MPa hydrogen and then another 0.69 MPa hydrogen was added and kept in contact with the reactants for 15 min. before venting. About half the final amount of hydrogen was added at room temperature, the reaction mixture was then heated to the temperatures and pressures shown in the Tables for 16 hrs. Examples 1–22 in Table 1 were done without a solvent. In Examples 23–31, Table 2, the solvent was $H_2O$ (50 ml), the quantity of phthalic anhydride used was 10 g and the reaction time was 4 hrs. unless otherwise noted. Table 3 lists comparative examples where the catalysts are not of this invention; the reactions were done neat and the reaction time was 16 hrs. unless otherwise noted.

Catalyst Preparation

The Pd/Re/C catalysts used were prepared as described in U.S. Pat. No. 4,609,636. Except for the substitution of 1/16" alumina extrusions or 20–30 mesh silica for carbon and not calcining these supports, the procedure used to prepare $Pd/Re/Al_2O_3$ or $Pd/Re/SiO_2$ was the same as described above. The Ru/Re/C, Rh/Re/C, or Pt/Re/C catalysts were prepared as described above except for the substitution of $RuCl_3 \cdot H_2O$, $RhCl_3 \cdot 3H_2O$, or $PtCl_4$ for $PdCl_2$.

A 5 weight percent Ru/0.2 weight percent Cu/$La_2O_3$ supported catalyst was prepared in the following manner. $La_2O_3$ (20 g) was added to a solution of $RuCl_3 \cdot 3H_2O$ (2.42 g) and $CuCl_2 \cdot 2H_2O$ (0.11 g) in distilled $H_2O$ (12 ml). After 3 hrs. at room temperature the slurry was dried at 110° C. for 18 hrs. with frequent stirring. The resulting solid was reduced under flowing $H_2$ at 100 cc/min. and heated to 350° C. in 22 min. After passing $H_2$ over the solid for 5 hrs. at 350° C., the catalyst was cooled under $H_2$. The catalyst was then passivated in 1.5% $O_2$ in $N_2$ at RT for 18 hrs. before use.

A 2 weight percent $Ru/TiO_2$ supported catalyst was prepared in the following manner. Anatase $TiO_2$ (20.0 g) was added to a solution of $RuCl_3 \cdot 3H_2O$ (0.91 g) in distilled $H_2O$ (18 ml). After 3 hrs. at RT with occasional stirring the slurry was dried at 110° C. for 18 hrs. with frequent stirring. The catalyst was treated in the same manner as the Ru/Cu/La$_2$O$_3$ catalyst described above.

A 1 weight percent Pd/3 weight percent Re/TiO$_2$ supported catalyst was prepared as described in U.S. Pat. No. 4,609,636 except for the substitution of anatase TiO$_2$ for carbon. The following catalysts that were used are commercially available; 0.5% Pd/C, 5% Ru/C, and 5% Ru/Al$_2$O$_3$.

Analytical Procedure

Dioxane/water (4/1, 50 ml) was added to the reaction mixture. The resulting solution was analyzed by capillary gas chromatography using a Varian 3700 chromatograph equipped with a Hewlett-Packard 50 m×0.2 mm id capillary column with a 0.11 μm thick, cross-linked methyl silicone coating. Sample size was 0.8 μl. The column was temperature programmed by holding at 70° C. for 10 min. and then heating to 230° C. at 15° C./min. Initial peak identification was established with knowns and/or GC-MS analyses.

TABLE 1

| Example No. | Temp. °C. | Press MPa | Catalyst | FeCl$_3$ (g)$^3$ | % PA$^a$ Conv. | % Sel. to Phthalide |
|---|---|---|---|---|---|---|
| 1 | 150 | 5.17 | 3% Pd + 3% Re on Carbon | 0.06 | 65 | 93 |
| 2 | 150 | 6.89 | 1% Pd + 1% Re on Carbon | 0.02 | 51 | 92 |
| 3 | 150 | 6.89 | 3% Pd + 3% Re on Carbon | 0.06 | 86 | 81 |
| 4 | 200 | 5.17 | 1% Pd + 3% Re on Al$_2$O$_3$ | 0.02 | 26 | 82 |
| 5$^b$ | 200 | 5.17 | 3% Pd + 3% Re on Carbon | 0.06 | 26 | 29 |
| 6 | 200 | 5.17 | 0.5% Pd on Carbon$^c$ | 0.01 | 58 | 65 |
| 7 | 200 | 5.17 | 1% Pd + 4% Re on Carbon | 0.06 | 69 | 85 |
| 8 | 200 | 5.17 | 1% Pd + 3% Re on SiO$_2$ | 0.06 | 66 | 92 |
| 9 | 200 | 5.17 | 3% Pd + 3% Re on Carbon | 0.06 | 87 | 77 |
| 10 | 200 | 5.17 | 3% Pd + 6% Re on Carbon | 0.06 | 76 | 86 |
| 11 | 200 | 5.17 | 1% Pd + 1% Re on Carbon | 0.02 | 78 | 89 |
| 12$^d$ | 200 | 5.17 | 1% Pd + 1% Re on Carbon | 0.02 | 68 | 92 |
| 13$^{d,e}$ | 200 | 5.17 | 1% Pd + 1% Re on Carbon | 0.008 | 55 | 88 |
| 14 | 150 | 5.17 | 1% Pd + 1% Re on Carbon | 0.004 | 40 | 89 |
| 15 | 150 | 5.17 | 1% Ru + 3% Re on Carbon | 0.02 | 23 | 86 |
| 16 | 150 | 5.17 | 1% Rh + 3% Re on Carbon | 0.02 | 8 | 71 |
| 17 | 150 | 5.17 | 1% Pt + 3% Re on Carbon | 0.02 | 7 | 80 |
| 18 | 150 | 5.17 | 5% Ru + .2% Cu on La$_2$O$_3$ | — | 8 | 70 |
| 19 | 200 | 5.17 | 5% Ru + 2% Ag on SiO$_2$ | — | 82 | 60 |
| 20 | 150 | 5.17 | 2% Ru on TiO$_2$ | — | 49 | 19 |
| 21 | 150 | 5.17 | 1% Pd + 3% Re on TiO$_2$ | — | 42 | 62 |
| 22 | 150 | 5.17 | 1% Ru + 3% Re on Carbon | — | 23 | 82 |

$^a$PA = Phthalic Anhydride
$^b$2 hrs. reaction time
$^c$Commercial catalyst
$^d$4 hrs. reaction time
$^e$40 g PA

TABLE 2

| Example No. | Temp. °C. | Press MPa | Catalyst | FeCl$_3$ (g)$^3$ | % PA$^a$ Conv. | % Sel. to Phthalide |
|---|---|---|---|---|---|---|
| 23$^b$ | 130 | 6.89 | 1% Pd + 3% Re on TiO$_2$ | — | 24 | 69 |
| 24 | 250 | 13.8 | 3% Pd + 6% Re on Carbon | 0.10$^c$ | 92 | 44 |
| 25 | 250 | 6.89 | 3% Pd + 6% Re on Carbon | 0.06 | 70 | 46 |
| 26 | 150 | 5.17 | 1% Pd + 1% Re on Carbon | 0.02 | 43 | 87 |
| 27 | 150 | 5.17 | 3% Pd + 6% Re on Carbon | 0.06 | 35 | 73 |

TABLE 2-continued

| Example No. | Temp. °C. | Press MPa | Catalyst | FeCl₃ (g)[3] | % PA[a] Conv. | % Sel. to Phthalide |
|---|---|---|---|---|---|---|
| 28 | 150 | 5.17 | 3% Pd + 6% Re on Carbon | 0.10[c] | 21 | 84 |
| 29 | 150 | 5.17 | 1% Pd + 1% Re on Carbon | 0.02 | 28 | 85 |
| 30 | 150 | 5.17 | 1.5% Pd + 3% Re on Carbon | 0.02 | 24 | 84 |
| 31 | 150 | 5.17 | 1% Pd + 3% Re TiO₂ | — | 38 | 83 |

[a]PA = Phthalic Anhydride
[b]6 hrs. reaction time
[c]Used Ferrous Sulfate

TABLE 3

| Example No. | Temp. °C. | Press MPa | Catalyst[a] | % PA[b] Conv. | % Sel. to Phthalide |
|---|---|---|---|---|---|
| 1[c] | 140 | 5.17 | 5% Ru on Carbon | 98 | <1 |
| 2 | 150 | 5.17 | 5% Ru on Carbon | 96 | <1 |
| 3 | 200 | 5.17 | 5% Ru on Carbon | 100 | <1 |

[a]These catalysts were commercially available.
[b]PA = Phthalic Anhydride
[c]11 hrs. reaction time The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of esters or lactones, comprising, in the presence of a catalyst, reacting hydrogen and an acyclic or cyclic carboxylic anhydride of the formula

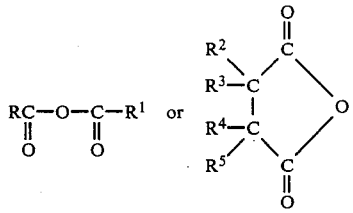

to form an ester of the formula

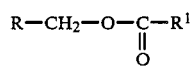

or a lactone of the formula

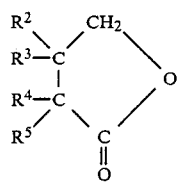

wherein R and $R^1$ independently are lower alkyl or cycloalkyl; $R^2$, $R^3$, $R^4$ and $R^5$ independently are hydrogen, lower alkyl, cycloalkyl or aryl; and wherein $R^3$ and $R^4$ taken together may form a saturated or unsaturated ring or an aromatic ring,
wherein the catalyst comprises:
(a) at least one group VIII metal, Re and Fe;
(b) at least one group VIII metal on a TiO₂ support;
(c) Ru and at least one of Re, Ag or Cu; or
(d) Pd and Fe on carbon.

2. A process according to claim 1, wherein in (a), (c) or (d) the catalyst support is carbon, Al₂O₃, SiO₂, TiO₂ or La₂O₃.

3. A process according to claim 1, wherein the catalyst is Pt/Re/Fe or Pd/Fe.

4. A process according to claim 3, wherein the catalyst is supported on carbon.

5. A process according to claim 1, wherein the catalyst is Pd on TiO₂.

6. A process according to claim 1, wherein the catalyst is Ru on TiO₂.

7. A process according to claim 1, wherein the catalyst is Ru/Ag on SiO₂.

8. A process according to claim 1, wherein the catalyst comprises:
(a) about 0.1-10% by weight of at least one group VIII metal, about 0.2-10% by weight of Re and about 0.001-1% by weight of Fe;
(b) about 0.1-20% by weight of at least one group VIII metal on a TiO₂ support;
(c) about 0.5-5% by weight of Ru and about 1-9% by weight of Re, or about 0.1-20% by weight of Ru and about 0.01-50% by weight of Ag or Cu; or
(d) about 0.02-10% by weight of Pd and about 0.001-1% by weight of Fe.

9. A process according to claim 1, wherein the carboxylic anhydride is phthalic anhydride.

10. A process according to claim 1, wherein the reaction is conducted in the presence of an aqueous solvent.

11. A process according to claim 1, wherein the reaction is conducted in the presence of a solvent which is water or a C₁₋₄-alcohol.

12. A process according to claim 1, wherein the reaction is conducted in the absence of a solvent.

13. A process according to claim 1, wherein the reaction temperature is about 100°-300° C.

14. A process according to claim 1, wherein the reaction temperature is about 150°-250° C.

15. A process according to claim 1, wherein the hydrogen is supplied at a pressure of about 0.45-17.3 MPa.

16. A process according to claim 1, wherein the hydrogen is supplied at a pressure of about 3.4-5.3 MPa.

17. A process according to claim 1, wherein the reaction is conducted for 0.25-48 hours.

18. In a process for the production of esters or lactones, comprising in the presence of a catalyst, reacting hydrogen and an acyclic or cyclic carboxylic anhydride to form the corresponding ester or lactone,
the improvement wherein the catalyst is:

(a) a group VIII metal, Re and Fe;
(b) a group VIII metal on a $TiO_2$ support;
(c) Ru and at least one of Re, Ag or Cu; or
(d) Pd and Fe on carbon.

* * * * *